US00PP26611P3

(12) United States Plant Patent
Sills et al.

(10) Patent No.: US PP26,611 P3
(45) Date of Patent: Apr. 19, 2016

(54) BLACKBERRY PLANT NAMED 'DRISBLACKTEN'

(50) Latin Name: ***Rubus* L. Subgenus *Rubus***
Varietal Denomination: DrisBlackTen

(71) Applicant: DRISCOLL STRAWBERRY ASSOCIATES, INC., Watsonville, CA (US)

(72) Inventors: Gavin R. Sills, Gilroy, CA (US); Andrea M. Pabon, Gilroy, CA (US)

(73) Assignee: DRISCOLL STRAWBERRY ASSOCIATES, INC., Watsonville, CA (US)

( * ) Notice: Subject to any disclaimer, the term of this patent is extended or adjusted under 35 U.S.C. 154(b) by 100 days.

(21) Appl. No.: 14/121,217

(22) Filed: Aug. 12, 2014

(65) Prior Publication Data

US 2016/0050820 P1 Feb. 18, 2016

(51) Int. Cl.
*A01H 5/00* (2006.01)

(52) U.S. Cl.
USPC ..... Plt./203

(58) Field of Classification Search
USPC ..... Plt./203
See application file for complete search history.

*Primary Examiner* — Annette Para
(74) *Attorney, Agent, or Firm* — Jondle & Associates, P.C.

(57) ABSTRACT

This invention relates to a new and distinct variety of blackberry plant named 'DrisBlackTen', particularly characterized by high productivity, large, black berries and self-fruitful plants, is disclosed.

2 Drawing Sheets

Genus and species: *Rubus* L. subgenus *Rubus*.
Variety denomination: 'DrisBlackTen'.

BACKGROUND OF THE NEW PLANT

The present invention relates to a new and distinct blackberry cultivar designated 'DrisBlackTen' and botanically known as *Rubus* L. subgenus *Rubus*. This new blackberry variety was identified in Santa Cruz County, Calif. in September 2006 and originated from a cross between the proprietary female parent blackberry plant 'BK294 (460G1)' (unpatented) and the proprietary male parent blackberry plant 'APF40' (unpatented). The original seedling of the new cultivar was first asexually propagated by tissue culture and root cuttings at a nursery in Santa Cruz County, Calif. 'DrisBlackTen' was subsequently asexually propagated by tissue culture and root cuttings and underwent further testing at a nursery in Santa Cruz County, Calif. from 2006 to 2011. The present invention has been found to be stable and reproduce true to type through successive asexual propagations.

Plant Breeder's Rights for this variety have not been applied for. 'DrisBlackTen' has not been made publicly available or sold anywhere in the world more than one year prior to the filing date of this application.

SUMMARY OF THE INVENTION

The following are the most outstanding and distinguishing characteristics of this new cultivar when grown under normal horticultural practices in Santa Cruz County, Calif.

1. High productivity;
2. Large, black berries; and
3. Self-fruitful plants.

DESCRIPTION OF THE PHOTOGRAPHS

This new blackberry plant is illustrated by the accompanying photographs which show the plant's canes, flowers, fruit, and leaves. The colors shown are as true as can be reasonably obtained by conventional photographic procedures. The photographs are of plants that are 2 years old.

Figure 1:
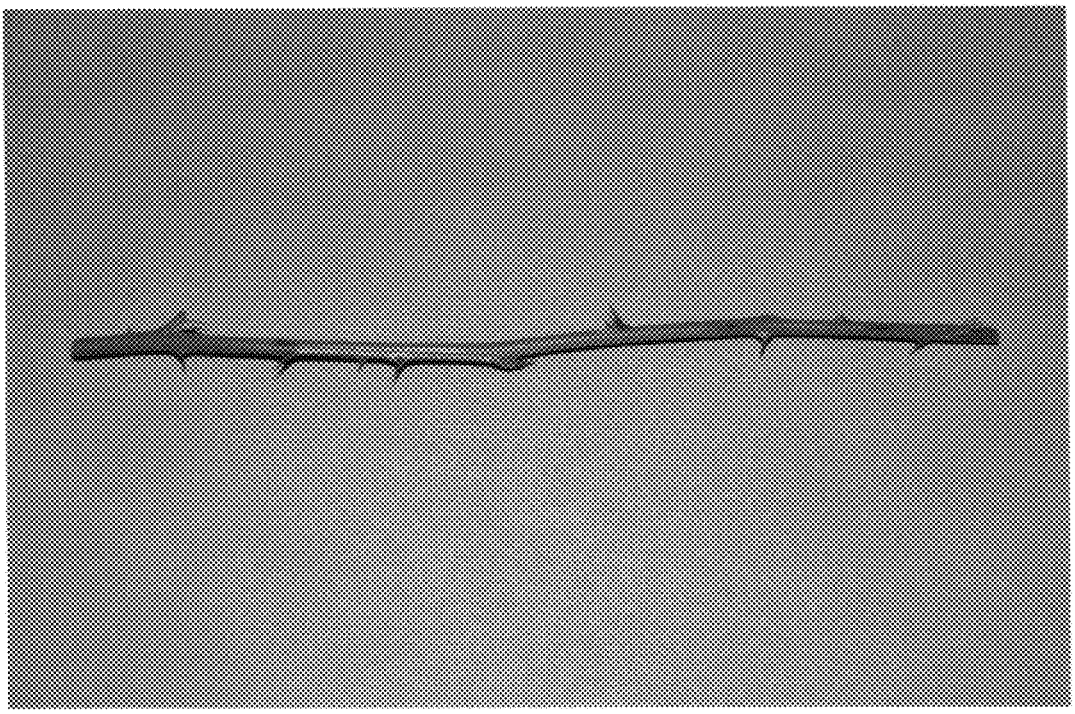
Figure 2:
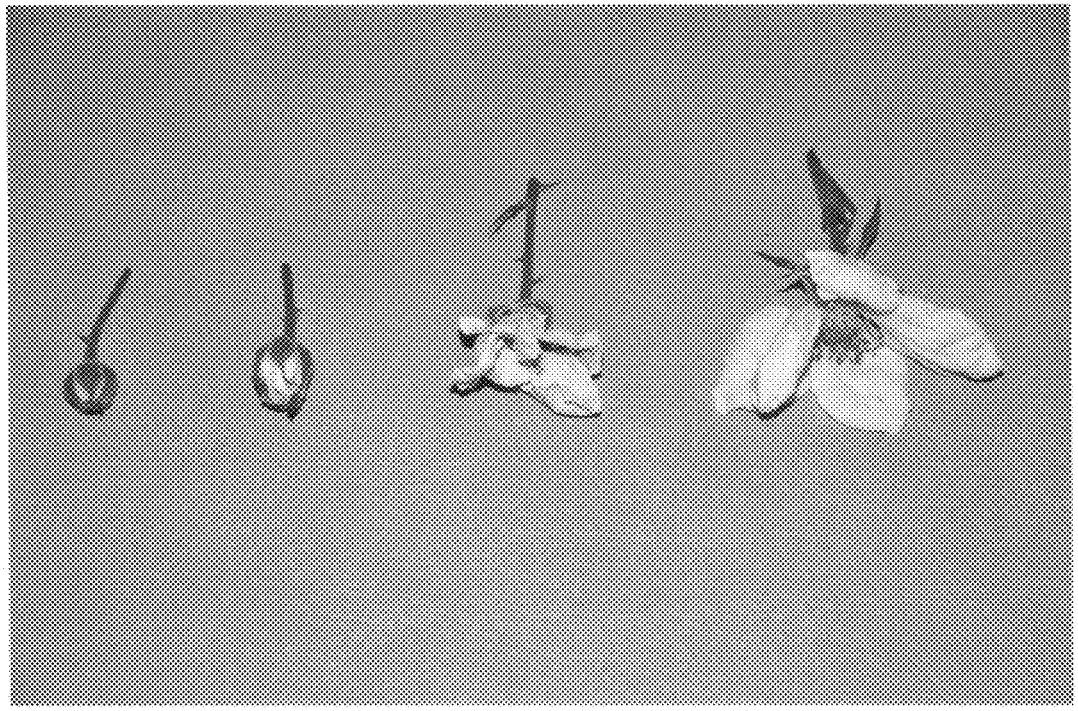
Figure 3:
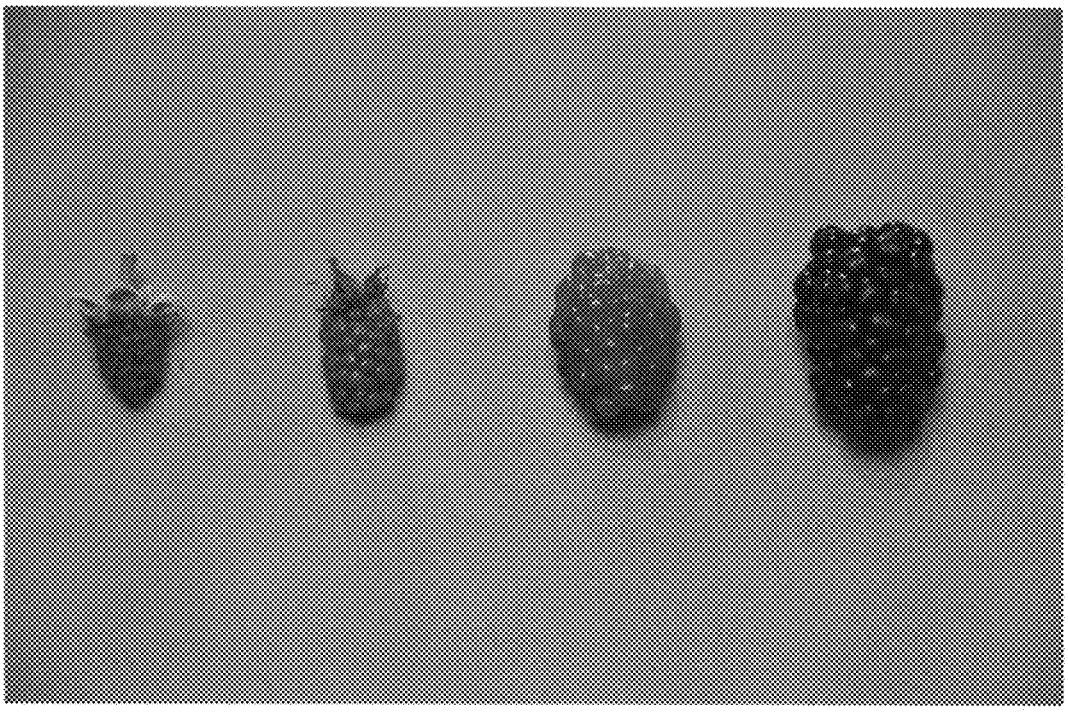
Figure 4:
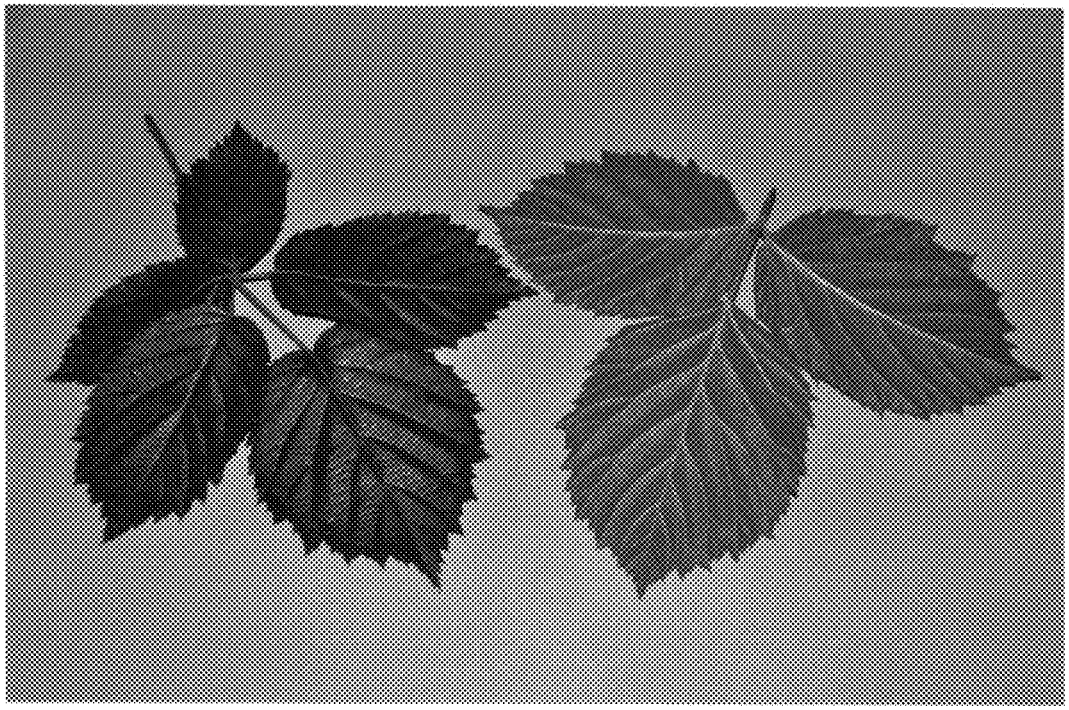

FIG. 1 shows a section of a young cane with spines.
FIG. 2 shows the flowers at various stages.
FIG. 3 shows the fruit at various stages
FIG. 4 shows the upper and lower surfaces of the leaves.

DESCRIPTION OF THE NEW VARIETY

The following descriptions of 'DrisBlackTen' are based on observations made in Santa Cruz County, Calif. on 2-year old plants. This description is in accordance with UPOV terminology. Color designations, color descriptions, and other phenotypical descriptions may deviate from the stated values and descriptions depending upon variation in environmental, seasonal, climatic and cultural conditions. 'DrisBlackTen' has not been observed under all possible environmental conditions. Color terminology follows The Royal Horticultural Society Colour Chart, London (R.H.S.) (2007 edition). Descriptive terminology is from the *Plant Identification Terminology, An Illustrated Glossary* 2$^{nd}$ edition, by James G. Harris and Melinda Woolf Harris, unless where otherwise defined.

DETAILED BOTANICAL DESCRIPTION

Classification:
*Family*.—Rosaceae.
*Botanical*.—*Rubus* L. subgenus *Rubus*.
*Common name*.—Blackberry.
*Variety name*.—'DrisBlackTen'.

Parentage:
*Female parent*.—Proprietary blackberry plant named 'BK294 (460G1)' (unpatented).
*Male parent*.—Proprietary blackberry plant named 'APF40' (unpatented).

Plant:

*Vigor*.—Medium.

*Growth habit*.—Upright to semi-upright.

*Productivity*.—High.

*Propagation*.—Tissue culture and root cuttings.

*Self-fruitfulness*.—Self-fruitful.

*Time of bud burst*.—Late.

Canes:

*Fruiting lateral length* (*4th lateral from tip*).—Short to medium; 31.8 cm.

*Number of fruit per lateral*.—10.3.

*Fruiting on current year's cane*.—Present.

*Cane internodal distance*.—4.4 cm.

*Number of new canes during flowering*.—Medium.

*New cane strength* (*observed full-grown shoot after picking*).—Strong.

*Glaucosity observed on full-grown shoot after picking*.—Weak.

*Young shoots*.—Quantity: Medium. Time of emergence from soil: Early. Anthocyanin coloration (during rapid growth): Very strong; RHS 59A (Dark red-purple). Intensity of green color: Medium; RHS 144B (Medium yellow-green). Number of glandular hairs: Many.

*Dormant cane*.—Length: Medium; 10.2 feet. Diameter (in central third): Medium; 9.68 mm. Cross section (from mid cane observed at end of first growing season): Angular. Color: RHS 144B (Medium yellow-green) and RHS 59A (Dark red-purple). Number of branches: Medium; Avg. 7.8. Distribution of branches: Over whole length. Anthocyanin coloration: Medium; RHS 59A (Dark red-purple). Spines: Number of spines: Many; 29. Size: Medium to large; 9.11 mm. Color: RHS 144A (Medium yellow-green). Density (on central third of cane): Medium. Texture: Medium to heavy. Attitude of apex in relation to cane: Downwards.

Leaves:

*Type*.—Odd-pinnate.

*Predominant number of leaflets*.—Three.

*Overlapping or relative position of lateral leaflets*.—Touching.

*Color*.—Upper surface: Dark; RHS 147A (Dark yellow-green). Lower surface: Light to medium; RHS 146A (Medium yellow-green).

*Glossiness of upper side*.—Weak.

*Cross section profile*.—Concave (margins rolled inwards).

*Leaflets*.—Shape: Oval. Margin: Doubly serrate. Depth of incisions: Medium. Type of incision margin: Bi-serrate. Apex: Truncate. Base: Obtuse. Rachis length between terminal leaflet and adjacent lateral leaflet: 7.6 mm.

*Lateral leaflet* (*basal pair*).—Length: 60.1 mm. Width: 38.2 mm. Length/width ratio: 1.6.

*Terminal leaflet*.—Length: Medium to long; 87.2 mm. Width: Medium; 56.2 mm. Length/width ratio: 1.6. Lobing: Absent. Undulation of margin (rippling of margin): Weak to medium. Blistering between veins (rugosity): Medium. Shape: Oval to slightly ovate. Tip: Truncate. Base: Obtuse. Margin: Doubly serrate. Cross-section: U-shaped.

*Petiole*.—Length: 1.2 cm. Diameter: 1.3 mm. Pigmentation: Upper surface: Medium; RHS 146B (Medium yellow-green). Lower surface: Medium; RHS 146D (Medium yellow-green).

*Stipule*.—Size: Small. Orientation: Erect.

Inflorescence:

*Time of beginning of flowering on previous year's cane*.—Early.

*Time of beginning of flowering on current year's cane*.—Very late.

*Flower diameter*.—Large; 43.89 mm.

*Flower number* (*at 3rd node from tip of lateral*).—7.

*Petal*.—Length: 23.83 mm. Width: 14.12 mm. Length/width ratio: 1.7. Color: RHS NN158B (White).

*Pedicel*.—Length: 27.33 mm. Diameter: 1.31 mm.

Fruit:

*Time of ripening on previous year's cane*.—Early.

*Time of ripening on current year's cane*.—Very late.

*Harvest interval*.—Mid-September to mid-November.

*Color*.—Immature: RHS 144A (Medium yellow-green). Maturing: RHS 46A (Dark red). Mature: RHS 203B (Black).

*Glossiness*.—Medium.

*Shape in longitudinal section*.—Medium ovate.

*Size*.—Large.

*Length*.—Medium; 27.44 mm.

*Width*.—Medium to broad; 21.31 mm.

*Ratio of length to width*.—Medium; 1.3.

*Weight* (*g/fruit*).—2.6774 g.

*Soluble solids* (%) (*in Brix*).—10.8.

*Titratable acidity*.—(% as citric acid).—1.1.

*Seed weight* (*g/seed*).—0.0029.

*Number of druplets/fruit*.—Medium; 91.

*Size of druplet*.—Medium.

*Firmness*.—Medium.

*Yield*.—Low to medium.

Disease, pest, and stress resistance: Not tested.

COMPARISON WITH PARENTAL AND COMMERCIAL VARIETIES

'DrisBlackTen' differs from the proprietary female parent 'BK294 (460G1)' (unpatented) in that 'DrisBlackTen' has better flavour and firmer, larger fruit than 'BK294 (460G1)'. Additionally, 'DrisBlackTen' is much less susceptible to red berry mite than 'BK294 (460G1)'.

DrisBlackTen' differs from the proprietary male parent 'APF40' (unpatented) in that 'DrisBlackTen' has slightly larger fruit than 'APF40'.

'DrisBlackTen' differs from the commercial variety 'Driscoll Carmel' (U.S. Plant Pat. No. 15,058) in that 'DrisBlackTen' has an upright to semi-upright growth habit and has three leaflets, whereas 'Driscoll Carmel' has a semi-erect growth habit and usually has five leaflets. Additionally, 'DrisBlackTen' has medium glossy, large sized fruit, whereas 'Driscoll Carmel' has strongly glossy, medium sized fruit.

'DrisBlackTen' differs from commercial variety 'Driscoll Eureka' (U.S. Plant Pat. No. 14,765) in that 'DrisBlackTen' has an upright to semi-upright growth habit and a late time of bud burst, whereas 'Driscoll Eureka' has a semi-erect growth habit and an early time of bud burst. Additionally, 'DrisBlackTen' has medium glossy, large sized fruit, whereas 'Driscoll Eureka' has strongly glossy, medium sized fruit.

We claim:

1. A new and distinct variety of blackberry plant named 'DrisBlackTen' as described and shown herein.

* * * * *